US007056702B2

(12) United States Patent
Villanueva et al.

(10) Patent No.: US 7,056,702 B2
(45) Date of Patent: Jun. 6, 2006

(54) DETECTING LIPOCALIN

(76) Inventors: Julie M. Villanueva, 205 Mead Rd., Decatur, GA (US) 30030; Stephen Quirk, 545 Morton Mill Ct., Alpharetta, GA (US) 30022

( * ) Notice: Subject to any disclaimer, the term of this patent is extended or adjusted under 35 U.S.C. 154(b) by 0 days.

(21) Appl. No.: 10/320,732

(22) Filed: Dec. 16, 2002

(65) Prior Publication Data

US 2004/0115728 A1    Jun. 17, 2004

(51) Int. Cl.
| C12P 21/08 | (2006.01) |
| C07K 14/00 | (2006.01) |
| A61K 39/395 | (2006.01) |
| C07H 21/04 | (2006.01) |
| C12N 5/12 | (2006.01) |

(52) U.S. Cl. .................. 435/70.21; 435/70.2; 435/326; 435/327; 435/328; 435/329; 435/330; 435/331; 435/332; 424/130.1; 530/350; 536/23.53; 536/23.5; 514/23; 514/24; 514/44

(58) Field of Classification Search ............... 435/70.2, 435/70.21, 326–332; 530/350; 536/23.53, 536/23.5; 424/130.1; 514/44, 24, 23
See application file for complete search history.

(56) References Cited

U.S. PATENT DOCUMENTS

| 4,036,945 | A |   | 7/1977 | Haber ....................... 424/1.49 |
| 4,331,647 | A |   | 5/1982 | Goldenberg ............... 424/1.37 |
| 4,816,567 | A |   | 3/1989 | Cabilly et al. ............ 530/387.3 |
| 4,946,778 | A |   | 8/1990 | Ladner et al. ............. 435/69.6 |
| 5,077,210 | A |   | 12/1991 | Eigler et al. ............... 435/176 |
| 5,627,034 | A | * | 5/1997 | Gould et al. ................. 435/6 |
| 5,750,373 | A |   | 5/1998 | Garrard et al. ............ 435/69.4 |
| 5,866,432 | A |   | 2/1999 | Sorsa et al. ................. 436/514 |
| 6,020,163 | A |   | 2/2000 | Conklin ..................... 435/69.1 |
| 6,114,123 | A |   | 9/2000 | Murry et al. ................. 435/6 |
| 6,136,526 | A | * | 10/2000 | Venge ........................ 435/4 |
| 6,143,720 | A |   | 11/2000 | Conklin ...................... 514/12 |
| 6,290,957 | B1 |   | 9/2001 | Lowman et al. ......... 424/133.1 |
| 6,365,716 | B1 |   | 4/2002 | Conklin ................... 530/387.9 |
| 2002/0128194 | A1 | * | 9/2002 | Green et al. ................ 514/12 |

FOREIGN PATENT DOCUMENTS

| EP |       404097 |   | 6/1990 |
| EP |       756708 | * | 7/2001 |
| WO | WO-931161 |   | 6/1993 |
| WO | WO-0188134 |   | 11/2001 |

OTHER PUBLICATIONS

J Biol Chem. May 15, 1993; 268(14): 10425-32).*
Eichler et al , Eur.Respir.J 1999, 14: 1145-1149.*
Goetz et al Biochemistry, 39 (8), 1935-1941, 2000.*
Kjeldsen L et al Blood. Feb. 1, 1994; 83(3): 799-807.*
Skerra, A. (2000). Biochim. Biophys. Acta, 1482, 337-350.*
Ganfornina et al Molecular Biology and Evolution 17:114-126 (2000).*
Flower, D. R et al (2000). Biochim. Biophys. Acta, 1482, 9-24.*
Blaser, J., et al., "A Sandwich Enzyme Immunoassay for the Determination of Neutrophil Lipocalin in Body Fluids", *Clinica Chemica Acta*, 235. (Feb. 1995),137-145.
Goetz, D. H., et al., "Ligand Preference Inferred from the Structure of Neutrophil Gelatinase Associated Lipocalin", *Biochemistry*, 39, (Feb. 2000), 1935-1941.
Logdberg, et al., "Immunocalins: A Lipocalin Subfamily that Modulates Immune and Inflammatory Responses", *Biochemica et Biophysica Acta*, 1482. (Feb. 2000), 284-297.
Xu, S. Y., et al., "Lipocalins as Biochemical Markers of Disease", *Biochemica et Biophysica Acta*, 1482. (Feb. 2000), 298-307.
Xu, S. Y., "Serum measurement of Human Neutrophil Lipocalin (HNL) Descriminate between Acute Bacterial and Viral Infections", *Scand. J. Clin. Lab. Invest.*, 55. (Feb. 1995), 125-131.
Xu, S. Y., et al., "The development of an assay for human neutrophil lipocalin (HNL)- to be used as a specific marker of neutrophil activity in vivo and in vitro", *Journal of Immunological Methods*, 171. (Feb. 1994), 245-252.
Andersson, K., et al., "Identification and optimization of regeneration conditions for affinity-based biosensor assays, a multivariant cocktail approach", *Anal. Chem.*, 71, (1999), 2475-2481.
Axelsson, L., et al., "Studies of the Release and Turnover of a Human Neutrophil Lipocalin", *Scandinavian Journal of Clinical and Laboratory Investigation*, 55. (1995) ,577-588.
Baines, Michael G., et al., "Purification of Immunoglobulin G (IgG)", *Methods in Molecular Biology*, 10, Humana Press,(1992),79-104.
Bird, et al., *Science*, 242. 242,(1988), 423-426.
Blaser, Jorg, et al., "A Sandwich Enzyme Immunoassay for the Determination of Neutrophil Lipocalin in Body Fluids", *Clinica Chimica Acta*, 235. (1995), 137-145.
Chothia, Cyrus, et al., "Domain association in immunoglobulin molecules. The packing of variable domains.", *Journal of Molecular Biology.* 186(3), (1985), 651-663.
Clackson, Tim et al., "Making antibody fragments using phage display libraries", *Nature.* 352 (6336). (1991), 624-628.

(Continued)

*Primary Examiner*—Lynette R. F. Smith
*Assistant Examiner*—Padma Baskar
(74) *Attorney, Agent, or Firm*—Schwegman, Lundberg, Woessner & Kluth, P.A.

(57) ABSTRACT

The invention provides antibodies reactive with distinct lipocalin epitopes that are useful for detecting inflammation and bacterial infections in mammals.

1 Claim, 2 Drawing Sheets

OTHER PUBLICATIONS

Cole, Thomas B., et al., "Hematologic alterations during acute infection in children with sickle cell disease.", *Pediatric Infectious Disease Journal. 6(5).* (1987), 454-457.

Coligan, et al., "Production of Polyclonal Antisera in Rabbits, Rats, Mice, and Hamsters", *Current Protocols in Immunology*, Section 2.4.1, (1992).

Coligan, et al., "Production of Polyclonal Antisera in Rabbits, Rats, Mice, and Hamsters", *Current Protocols in Immunology*, Sections 2.5.1-2.6.7, (1992).

Coligan, et al., "Production of Polyclonal Antisera in Rabbits, Rats, Mice, and Hamsters", *Current Protocols in Immunology*, Sections 2.7.1-2.7.12, (1992).

Coligan, et al., "Production of Polyclonal Antisera in Rabbits, Rats, Mice, and Hamsters", *Current Protocols in Immunology*, Sections 2.9.1-2.9.3, (1992).

Coligan, et al., "Unit 9", *Current Protocols in Immunology*, Wiley Interscience, (1991).

Cunningham, Brian C., et al., "Production of an atrial natriuretic peptide variant that is specific for type A receptor", *EMBO J 1994 Jun. 1:13(11).* (1994), 2508-2515.

Eichler, I., et al., "Human Neutrophil Lipocalin, a Highly Specific Marker for Acute Exacerbation in Cystic Fibrosis", *European Respiratory Journal*, 14, (1999), 1145-1149.

Flower, Darren R., "Multiple molecular recognition properties of the lipocalin protein family", *J Mol Recognit 1995 May-Jun.:8(3)*, (1995), 185-195.

Flower, Darren R., "The lipocalin protein family: a role in cell regulation", *FEBS Letters*, 354(1). (1994), 7-11.

Friedl, A., et al., "Neutrophil Gelatinase-associated Lipocalin in Normal and Neoplastic Human Tissues. Cell Type-specific Pattern of Expression", *The Histochemical Journal*, 31, (1999), 433-441.

Goetz, David H., et al., "Ligand Preference Inferred from the Structure of Neutrophil Gelatinase Associated Lipocalin", *Biochemistry*, 39. (2000), 1935-1941.

Green, Jonathan A. and Margaret M. Manson , "Production of Polyclonal Antisera", *Immunochemical Protocols*, Manson, ed., Humana Press, (1992), 1-5.

Harlow, Ed and David Lane, *Antibodies: A Laboratory Manual*, Cold Spring Harbor Publication,(1988), 726.

Hawkins, Robert E., et al., "Selection of phage antibodies by binding affinity. Mimicking affinity maturation.", *Journal of Molecular Biology 226(3).* (1992), 889-896.

Henson, P. M., "The immunologic release of constituents from neutrophil leukocytes. I. The role of antibody and complement on nonphagocytosable surfaces or phagocytosable particles.", *Journal of Immunology. 107(6).* (1971), 1535-46.

Hollinger, P., et al., "Diabodies": small bivalent and bispecific antibody fragments., *Proceedings of the National Academy of Sciences of the United States of America. 90(14).* (1993), 6444-6448.

Holmes, M. A., et al., "Structural consequences of humanizing an antibody.", *Journal of Immunology. 158(5).* (1997), 2192-2201.

Johnsson, B., et al., "Immobilization of proteins to a carboxymethyldextran-modified gold surface for biospecific interaction analysis in surface plasmon resonance sensors.", *Analytical Biochemistry. 198(2).* (1991), 268-277.

Jones, P. T., et al., "Replacing the complementarity-determining regions in a human antibody with those from a mouse.", *Nature. 321 (6069)*, (1986), 522-525.

Kobayashi, H. and Ikada, Y., "Covalent Immobilization of Proteins Onto the Surface of Poly(vinil alchohol) Hydrogel", *Biomaterials. 12.* (1991), 747-751.

Kohler G. and Milstein C., "Continuous cultures of fused cells secreting antibody of predefined specificity.", *Nature. 256(5517).* (1975), 495-97.

Larrick, James W., et al., *Methods: a Companion to Methods in Enzymology*, vol. 2, (1991), 106.

Lash, Joseph A., et al., "Plasma lactoferrin reflects granulocyte activation in vivo.", *Blood. 61(5)*, (1983), 885-888.

Lofas, S. and Johnsson, B., "A Novel Hydrogel Matrix on Gold Surfaces in Surface Plasmon Resonance Sensors for Fast and Efficient Covalent Immobilization of Ligands", *J. Chem. Soc. Commun.*, Full Journal Name: Journal of the Chemical Society Chemical Communications,(1990), 1526-1528.

Logdberg, Lennart and Wester Lena , "Immunocallns: a lipocalln subfamily that modulates immune and inflammatory responses.", *Biophysica Acta. 1482(1-2).* (2000), 284-297.

Lowman, H. B., et al., "Selecting High-Affinity Binding Proteins by Monovalent Phage Display", *Biochemistry. 30 (45).* (Nov. 12, 1991), 10832-10838.

Marks, James D., et al., "By-passing immunization. Human antibodies from V-gene libraries displayed on phage.", *Journal of Molecular Biology. 222(3).* (1991), 581-597.

McDonnell, J. M., "Surface plasmon resonance towards an understanding of the mechanisms of biological molecular recognition", *Current Opinion Chemical Biology*, 5, (2001), 572-577.

Mellors, John W., et al., "A Simple Index to Identify Occult Bacterial Infection in Adults with Acute Unexplained Fever", *Archives of Internal Medicine*, 147, (1987), 666-671.

Morgan, H. and Taylor, D. M., "A Surface Plasmon Resonance Immunosensor Based on the Streptavidin-Biotin Complex", *Biosensors and Bioelectronics*, 7, (1992), 405-410.

Morrison, S. L., et al., "Chimeric human antibody molecules: mouse antigen-binding domains with human constant region domains.", *Proceedings of the National Academy of Sciences of the United States of America. 81(21):.* (1984), 6851-6855.

Myszka, D., "Kinetic analysis of macromolecular interactions using the surface plasmon resonance biosensors", *Curr. Opin. Biotechnol.*, 8, (1997), 50-57.

Novotny J. and Haber, E., "Structural invariants of antigen binding: comparison of immunoglobulin VL-VH and VL-VL domain dimers.", *Proceedings of the National Academy of Sciences of the United States of America. 82(14).* (1985), 4592-4596.

Ohlson, S. "Detection and characterization of weak affinity antibody antigen recognition with bimolecular interaction analysis", *J. Mol. Recognit.*, 10, (1997), 135-138.

Pack, P., et al., "Improved bivalent minlantibodies, with identical avidity as whole antibodies, produced by high cell density fermentation of *Escherichia coli*.", *Bio/Technology. 11(11)*, (1993), 1271-1277.

Pluckthun, A., "Antibodies from *Escherichia coli*", *The Pharmacology of Monoclonal Antibodies*, 113. Robenburg and Moore eds. Springer-Verlag, N.Y.,(1994), pp. 269-315.

Presta, Leonard G., "Antibody Engineering", *Current Opinion in Structural Biology*, 2. (1992), 593-596.

Riechmann, L., et al., "Reshaping human antibodies for therapy.", *Nature. 332(6162).* (1988), 323-327.

Schmekel, Birgitta, et al., "Myeloperoxidase in Human Lung Lavage I. A Marker of Local Neutrophil", *Inflammation*, 14 (4). (1990), 447-454.

Taylor, D. M., et al., "Characterization of chemisorbed monolayers by surface potential measurements.", *Journal of Physics D-Applied Physics*, vol. 24, No. 8, (1991), 1443-1450.

Vaswani, S. K., et al., ". Humanized antibodies as potential therapeutic drugs.", *Annals of Allergy. Asthma. & Immunology. 81(2)*. (1998), 105-115.

Venge, Per, "The Monitoring of Inflammation by Specific Cellular Markers", *Scandinavian Journal of Clinical and Laboratory Investigation*, 54. (1994), 47-54.

Whitlow, et al., *Methods; a Companion to Methods in Enzymology*. vol. 2, (1991), 97.

Xu, Shengyan, et al., "Lipocalins as Biochemical Markers of Desease", *Biochimica et Biophysica Acta. 1482.* (2000), 298-307.

Xu, S. Y., et al., "Serum Measurements of Human Neutrophil Lipocalin (HNL) Discriminate Between Acute Bacterial and Viral Infections", *Scandinavian Journal of Clinical and Laboratory Investigations. 55*, (1995), 125-131.

Xu, S. Y., et al., "The Development of an Assay for Human Neutrophil Lipocalin (HNL)—To Be Used As A Specific Marker of Neutrophil Activity in Vivo and Vitro", *Journal of Immunological Methods*, 171. (1994), 245-252.

* cited by examiner

SEQUENCE LISTING

<160> NUMBER OF SEQ ID NOS: 14

<210> SEQ ID NO 1
<211> LENGTH: 177
<212> TYPE: PRT
<213> ORGANISM: Homo sapiens

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

-continued

```
Gln Lys Met Tyr Ala Thr Ile Tyr Glu Leu Lys Glu Asp Lys Ser Tyr
     50                  55                  60
Asn Val Thr Ser Val Leu Phe Arg Lys Lys Cys Asp Tyr Trp Ile
 65                  70                  75                  80
Arg Thr Phe Val Pro Gly Cys Gln Pro Gly Glu Phe Thr Leu Gly Asn
                 85                  90                  95
Ile Lys Ser Tyr Pro Gly Leu Thr Ser Tyr Leu Val Arg Val Val Ser
                100                 105                 110
Thr Asn Tyr Asn Gln His Ala Met Val Phe Phe Lys Lys Val Ser Gln
            115                 120                 125
Asn Arg Glu Tyr Phe Lys Ile Thr Leu Tyr Gly Arg Thr Lys Glu Leu
        130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp
```

<210> SEQ ID NO 2
<211> LENGTH: 12
<212> TYPE: PRT
<213> ORGANISM: Homo sapiens
<400> SEQUENCE: 2

```
Pro Leu Gln Gln Asn Phe Gln Asp Asn Gln Phe Gln
 1               5                  10
```

<210> SEQ ID NO 3
<211> LENGTH: 14
<212> TYPE: PRT
<213> ORGANISM: Homo sapiens
<400> SEQUENCE: 3

```
Asn Ala Ile Leu Arg Glu Asp Lys Asp Pro Gln Lys Met Tyr
 1               5                  10
```

<210> SEQ ID NO 4
<211> LENGTH: 4
<212> TYPE: PRT
<213> ORGANISM: Homo sapiens
<400> SEQUENCE: 4

```
Lys Glu Asp Lys
 1
```

<210> SEQ ID NO 5
<211> LENGTH: 4
<212> TYPE: PRT
<213> ORGANISM: Homo sapiens
<400> SEQUENCE: 5

```
Arg Lys Lys Lys
 1
```

<210> SEQ ID NO 6
<211> LENGTH: 5
<212> TYPE: PRT
<213> ORGANISM: Homo sapiens
<400> SEQUENCE: 6

```
Gly Cys Gln Pro Gly
```

```
<210> SEQ ID NO 7
<211> LENGTH: 8
<212> TYPE: PRT
<213> ORGANISM: Homo sapiens

<400> SEQUENCE: 7

Gly Asn Ile Lys Ser Tyr Pro Gly
 1               5

<210> SEQ ID NO 8
<211> LENGTH: 4
<212> TYPE: PRT
<213> ORGANISM: Homo sapiens

<400> SEQUENCE: 8

Asn Tyr Asn Gln
 1

<210> SEQ ID NO 9
<211> LENGTH: 10
<212> TYPE: PRT
<213> ORGANISM: Homo sapiens

<400> SEQUENCE: 9

Phe Pro Val Pro Ile Asp Gln Cys Ile Asp
 1               5                  10

<210> SEQ ID NO 10
<211> LENGTH: 15
<212> TYPE: PRT
<213> ORGANISM: Homo sapiens

<400> SEQUENCE: 10

Cys Leu Ser Lys Val Pro Leu Gln Gln Asn Phe Gln Asp Asn Gln
 1               5                  10                  15

<210> SEQ ID NO 11
<211> LENGTH: 16
<212> TYPE: PRT
<213> ORGANISM: Homo sapiens

<400> SEQUENCE: 11

Cys Gly Asn Ala Ile Leu Arg Glu Asp Lys Asp Pro Gln Lys Met Tyr
 1               5                  10                  15

<210> SEQ ID NO 12
<211> LENGTH: 8
<212> TYPE: PRT
<213> ORGANISM: Homo sapiens

<400> SEQUENCE: 12

Tyr Glu Leu Lys Glu Asp Lys Ser
 1               5

<210> SEQ ID NO 13
<211> LENGTH: 14
<212> TYPE: PRT
<213> ORGANISM: Homo sapiens

<400> SEQUENCE: 13

Leu Ser Lys Val Pro Leu Gln Gln Asn Phe Gln Asp Asn Gln
 1               5                  10
```

```
<210> SEQ ID NO 14
<211> LENGTH: 15
<212> TYPE: PRT
<213> ORGANISM: Homo sapiens

<400> SEQUENCE: 14

Gly Asn Ala Ile Leu Arg Glu Asp Lys Asp Pro Gln Lys Met Tyr
 1               5                  10                  15
```

DETECTING LIPOCALIN

FIELD OF THE INVENTION

The present invention relates to the use of antibodies directed against specific regions of lipocalin for detecting infections in a mammal.

BACKGROUND OF THE INVENTION

Inflammation occurs as a result of tissue damage. This tissue damage can be from microbial invasion, autoimmune processes, tissue infection, allograft rejection, or such hurtful or destructive external influences as heat, cold, radiant energy, electrical or chemical stimuli, or mechanical trauma. Whatever the cause or bodily site, the inflammatory response is quite similar, consisting of a complicated set of functional and cellular adjustments, involving the microcirculation, fluid shifts, and inflammatory cells (leukocytes). When tissue damage occurs, soluble chemical substances are elaborated which initiate the inflammatory response.

The inflammatory response consists of a complex series of events that may be summarized as follows. (1) A local increase in blood flow, with capillary dilatation and increased permeability to the fluid components of the blood. (2) A localized exudation of fluid at the site of injury, including the proteins of the plasma that normally leave the capillaries at a relatively low rate. (3) The exudation of leukocytes from the capillaries into the inflammation site. This exudate initially consists primarily of polymorphonuclear leukocytes, followed by monocytes, lymphocytes, and plasma cells. These leukocytes produce a variety of mediators that control the extent and duration of the inflammatory response, and have a series of receptors on their surfaces available to react to the host of chemical mediators and proteins that are part of the inflammatory fluid. Such leukocyte receptor-mediator or protein interactions are important in controlling leukocyte function within the inflammatory site.

The identification and characterization inflammation is an important part of medical and veterinary practice. In the case of infectious causes of inflammation, it is frequently necessary to search for "hidden sites of inflammation" in individuals who present with clinical syndromes no more specific than fever and weight loss. Similarly, in patients with autoimmune disease such as rheumatoid arthritis or allograft rejection as causes of inflammation, identification of the site(s) and extent of inflammation and its changes with therapy are an important part of medical and veterinary practice. Not surprisingly, then, much effort has been expended and many techniques developed in an attempt to assess the site(s) and extent of the inflammatory process. These techniques include conventional x-ray techniques, computerized axial tomographic scanning (CAT scanning), and a variety of radionuclide scans. See Sutton, A Textbook of Radiology and Imaging, 3rd Ed., Churchill Livingston, 1980: Clinical Nuclear Medicine, Maysey et al., ed., W. B. Sanders, 1983.

One area of difficulty for medical practitioners involves distinguishing between bacterial and viral infections in patients that exhibit many symptoms of either type of infection (e.g. fever, flu-like symptoms, etc.). However, quick, reliable means for assessing whether anti-bacterial drug or an anti-viral drug should be administered are not available. Hence, new methods for distinguishing bacterial infections from viral infections are needed.

SUMMARY OF THE INVENTION

The invention provides an isolated antibody that can bind to a lipocalin antigen comprising any one of SEQ ID NO:2, SEQ ID NO:3, SEQ ID NO:4;SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14.

Such antibody preparations can be used to detect lipocalin. When heightened levels of lipocalin are detected in a mammal, the mammal may have a bacterial infection. Hence, the invention provides a method for detecting or predicting a bacterial infection in a subject. Such a method can include the following steps: (a) contacting a test sample with an isolated first antibody preparation that can bind to a lipocalin antigen comprising any one of SEQ ID NO:2, SEQ ID NO:3, SEQ ID NO:4;SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14;and (b) detecting whether an antigen-antibody complex forms between the antibody and lipocalin that is present in the test sample.

This method can further include contacting the antigen-complex with a second antibody preparation that can bind to a lipocalin antigen comprising any one of SEQ ID NO:2, SEQ ID NO:3, SEQ ID NO:4;SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14.

The method can also include determining the amount of lipocalin in the test sample.

The method can further include comparing the amount of lipocalin in the test sample with the amount of lipocalin in a control sample. For example, such a control sample can be a sample taken from a subject without a bacterial infection or the control sample can be a solution of lipocalin of known concentration.

The methods of the invention can involve any immunoassay procedure known to one of skill in the art. For example, the method can be an ELISA, a radioimmunoassay or a surface plasmin resonance procedure. Hence, in some embodiments, at least one antibody preparation is immobilized on a solid substrate.

The bacterial infection that may be detected can be caused by infection of *Aeromonas* spp., *Bacillus* spp., *Bacteroides* spp. *Campylobacter* spp., *Clostridium* spp., *Enterobacter* spp., *Enterococcus* spp., *Escherichia* spp., *Gastrospirillum* sp., *Helicobacter* spp., *Klebsiella* spp., *Salmonella* spp., *Shigella* spp., *Staphylococcus* spp., *Pseudomonas* spp., *Vibrio* spp., or *Yersinia* spp. The bacterial infection can also be associated with a staph infection, typhus, food poisoning, bascillary dysentery, pneumonia, cholera, an ulcer, diarrhea, hemorrhagic colitis, hemolytic uremic syndrome, or thrombotic thrombocytopenic purpura. The bacterial infection can further be caused by infection of *Staphylococcus aureus, Salmonella typhi, Escherichia coli, Escherichia coli* O157:H7, *Shigella dysenteria, Psuedomonas aerugenosa, Pseudomonas cepacia, Vivrio cholerae, Helicobacter pylori*, a multiply-resistant strain of *Staphylococcus aureus*, a vancomycin-resistant strain of *Enterococcus faecium*, or a vancomycin-resistant strain of *Enterococcus faecalis*.

The invention further provides a kit that includes an isolated first antibody preparation that can bind to a lipocalin antigen comprising any one of SEQ ID NO:2, SEQ ID NO:3, SEQ ID NO:4;SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO: 14, and instructions for detecting lipocalin.

The invention further comprises a kit for detecting lipocalin comprising instructions for detecting lipocalin, and a biosensor comprising a first antibody preparation that can bind a lipocalin peptide comprising any one of SEQ ID NO:2, SEQ ID NO:3, SEQ ID NO:4;SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14.

Instructions provided with the kits of the invention can comprise: (a) instructions for obtaining a test sample; (b) instructions for contacting the biosensor with the test sample; or (c) instructions for determining whether an antibody-antigen complex has formed between the first antibody preparation and lipocalin in the test sample.

The kits of the invention can further comprises a second antibody preparation that can bind to a lipocalin antigen comprising any one of SEQ ID NO:2, SEQ ID NO:3, SEQ ID NO:4;SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14. Such a second antibody can be labeled with a detectable substance.

The kit can further comprise a control sample. Such a control sample can be, for example, a sample taken from a subject without a bacterial infection or a lipocalin solution of known concentration.

DETAILED DESCRIPTION OF THE INVENTION

Figure 1:
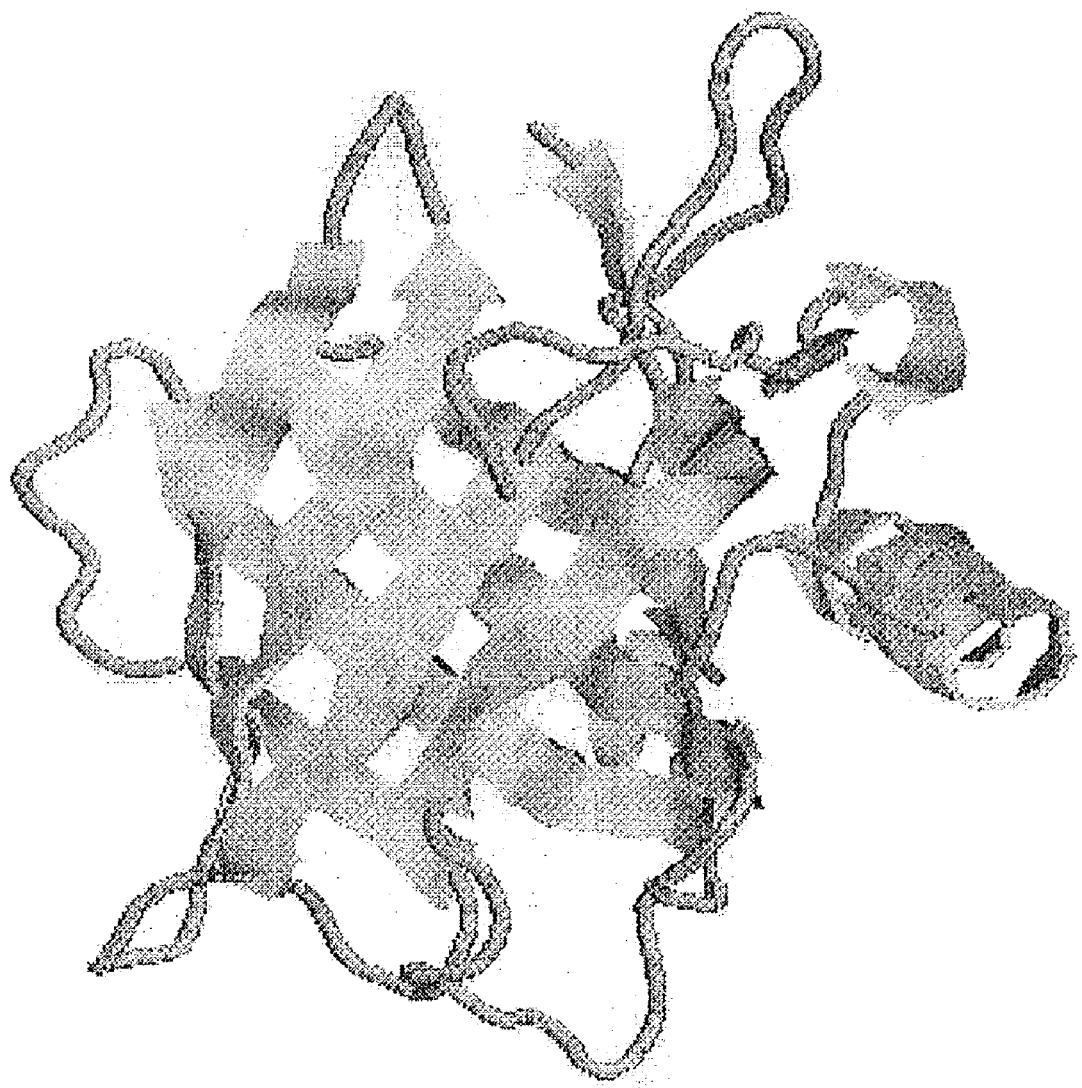
FIG. 1 illustrates the structural elements of lipocalin. The beta sheet secondary structural elements are shown as flat arrows. The loops are depicted as thin loop-like structures. The structure is derived from Protein Data Bank file 1DFV.ent.

The invention provides antibody preparations directed against lipocalin peptides of the invention, for example, against a loop region of lipocalin. Peptides contemplated by the invention include those having any one of SEQ ID NO:2–14 as well as variants and derivatives thereof Lipocalins Lipocalins are small molecular weight (10–100 kDa), secreted proteins that are believed to be involved in the transport of small, hydrophobic molecules. Lipocalins appear to have a regulatory influence on the inflammatory cascade and protect against excessive tissue damage (3, 4). The lipocalins are members of the superfamily known as calycins, all of which are ligand-binding proteins for hydrophobic molecules. Other members of the calycin family are fatty acid-binding proteins (FABPs) and avidins. The members of this super-family share some conformational homology, but little sequence homology (Flower, FEBS Letters 354:7–11, 1994;and Flower, J. Molec. Recognition 8:185–195, 1995).

The lipocalin family of proteins is characterized by structural motifs comprising a barrel formed by eight, anti-parallel, beta-sheets, which are arranged as two orthogonal sheets. The members of the lipocalin family of proteins are diverse at the sequence level. However, the most related members of the family share three characteristic conserved sequence motifs. Members of the closely related group of lipocalins include: retinol-binding protein, purpurin, retinoic acid-binding protein, $\alpha_{2u}$-globin, major urinary protein, bilin-binding protein, α-crustacyanin, pregnancy protein 14, β-lactoglobin, neutrophil lipocalin and choroid plexus protein. Lipocalins that have two or fewer conserved sequence motifs are classified as "outlier lipocalins." Outlier lipocalins include: odorant-binding protein, von Ebner's gland protein, probasin and aphrodisin.

The present invention relates to the use of human neutrophil lipocalin (HNL) as a diagnostic marker for identifying inflammation. Human neutrophil lipocalin is also known as N-formyl peptide binding protein, 25 kDa α2-microglobulin-related protein, and Neutrophil gelatinase associated lipocalin (NGAL). Human neutrophil lipocalin exists as a monomer (24 kDa), a homodimer, or a heterodimer with proteins such as gelatinase B or matrix metalloproteinase-9 (MMP-9).

Levels of human neutrophil lipocalin in the serum of healthy human subjects range from approximately 50–100 μg/L (5, 6). Serum HNL levels in patients with viral infections are similar to those found in healthy subjects (7). However, when a bacterial infection is present, the mean HNL concentration in serum has been shown to increase to ~350 μg/L (7). Thus, HNL can be used as a biomarker for a device that distinguishes between bacterial and viral infections.

Human neutrophil gelatinase-associated lipocalin can have the following amino acid sequence (SEQ ID NO:1).

```
  1 QDSTSDLIPA PPLSKVPLQQ NFQDNQFQGK WYVVGLAGNA

41 ILREDKDPQK MYATIYELKE DKSYNVTSVL FRKKKCDYWI

81 RTFVPGCQPG EFTLGNIKSY PGLTSYLVRV VSTNYNQHAM

121 VFFKKVSQNR EYFKITLYGR TKELTSELKE NFIRFSKSLG

161 LPENHIVFPV PIDQCID
```

Lipocalin contains eight surface-accessible loops. These areas are shown as thin bands in FIG. 1. Two of these loops flank the central lipocalin beta barrel. The loop areas make good epitope targets because they are solvent exposed. The sequences of the loop regions are as follows:

```
1. Pro17 to Gln28:   PLQQNFQDNQFQ    (SEQ ID NO: 2)

2. Asn39 to Tyr52:   NAILREDKDPQKMY  (SEQ ID NO: 3)

3. Lys59 to Ser63:   KEDK            (SEQ ID NO: 4)

4. Arg72 to Lys75:   RKKK            (SEQ ID NO: 5)

5. Gly86 to Gly90:   GCQPG           (SEQ ID NO: 6)

6. Gly95 to Gly102:  GNIKSYPG        (SEQ ID NO: 7)

7. Asn114 to Gln117: NYNQ            (SEQ ID NO: 8)

8. Phe168 to Asp177: FPVPIDQCID      (SEQ ID NO: 9)
```

Any peptide within SEQ ID NO:1–9 can be used as an antigen for generating polyclonal or monoclonal antibodies that are specific to lipocalin. In some embodiments, two opposing loops from different sides of the lipocalin molecule can be chosen such that the resulting antibodies can be used to capture lipocalin in a diagnostic assay, that is, they are capable of forming a sandwich structure. For example, antibodies against loops 1 (SEQ ID NO:2) and 2 (SEQ ID NO:3) or 4 (SEQ ID NO:5) and 5 (SEQ ID NO:6), could be employed. It may also be desirable to include one or two flanking residues on each side of smaller loops in order to increase their antigenicity (for example when using loop 3 (SEQ ID NO:4)).

Four loop regions (1, 2, 3, and 8) were initially picked to raise monoclonal antibodies. The specific peptides synthesized were as follows, with the positions of amino acids from lipocalin identified in parentheses:

```
Loop 1: CLSKVPLQQNFQDNQ  (residues 12 to 26)   (SEQ ID NO: 10)

Loop 2: CGNAILREDKDPQKMY (residues 37 to 52)   (SEQ ID NO: 11)

Loop 3: YELKEDKS         (residues 56 to 63)   (SEQ ID NO: 12)

Loop 8: FPVPIDQCID       (residues 168 to 177) (SEQ ID NO:  9)
```

Another set of peptides was chosen for conjugation to KLH protein. These peptides had the following sequences:

```
SEQ ID NO: 12 - YELKEDKS

SEQ ID NO: 13 - LSKVPLQQNFQDNQ

SEQ ID NO: 14 - GNAILREDKDPQKMY

SEQ ID NO:  9 - FPVPIDQCID
```

Antibody preparations obtained had strong IgG and a strong IgM responses, in particular, with the SEQ ID NO:9 and SEQ ID NO:11 peptides.

Antibodies

The invention provides antibody preparations directed against lipocalin peptides of the invention, for example, against a loop region of lipocalin. Peptides contemplated by the invention include those having any one of SEQ ID NO:2–14 as well as variants and derivatives thereof.

All antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651–66, 1985); Novotny and Haber, Proc. Natl. Acad. Sci. USA 82, 4592–4596 (1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4;IgA-1 and IgA-2. The heavy chains constant domains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely a adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector function, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody that includes the variable domain complementarity determining regions (CDR), and the like forms, all of which fall under the broad term "antibody," as used herein. The present invention contemplates the use of any specificity of an antibody, polyclonal or monoclonal, and is not limited to antibodies that recognize and immunoreact with a specific antigen. In preferred embodiments, in the context of both the therapeutic and screening methods described below, an antibody or fragment thereof is used that is immunospecific for an antigen or epitope of the invention.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments, which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Antibody fragments can retain an ability to selectively bind with the antigen or receptor and are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies, vol. 113, Rosenburg and Moore eds. Springer-Verlag, N.Y., pp. 269–315 (1994).

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097;WO 93/11161, and Hollinger et al., Proc. Natl. Acad Sci. USA 90: 6444–6448 (1993).

The preparation of polyclonal antibodies is well known to those skilled in the art. See, for example, Green, et al., Production of Polyclonal Antisera, in: *Immunochemical Protocols* (Manson, ed.), pages 1–5 (Humana Press); Coligan, et al., Production of Polyclonal Antisera in Rabbits, Rats Mice and Hamsters, in: *Current Protocols in Immunology*, section 2.4.1 (1992), which are hereby incorporated by reference.

The preparation of monoclonal antibodies likewise is conventional. See, for example, Kohler & Milstein, Nature, 256:495 (1975); Coligan, et al., sections 2.5.1–2.6.7; and Harlow, et al., in: *Antibodies: A Laboratory Manual*, page 726 (Cold Spring Harbor Pub. (1988)), which are hereby incorporated by reference. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1–2.7.12 and sections 2.9.1–2.9.3;Barnes, et al., Purification of Immunoglobulin G (IgG), in: *Methods in Molecular Biology*, Vol. 10, pages 79–104 (Humana Press (1992).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody indicates the character of the antibody as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al. Proc. Natl. Acad Sci. 81, 6851–6855 (1984).

Methods of in vitro and in vivo manipulation of monoclonal antibodies are well known to those skilled in the art. For example, the monoclonal antibodies to be used in accordance with the present invention may be made by the hybridoma method first described by Kohler and Milstein, Nature 256, 495 (1975), or may be made by recombinant methods, e.g., as described in U.S. Pat. No. 4,816,567. The monoclonal antibodies for use with the present invention may also be isolated from phage antibody libraries using the techniques described in Clackson et al. Nature 352: 624–628 (1991), as well as in Marks et al., J. Mol Biol. 222: 581–597 (1991). Another method involves humanizing a monoclonal antibody by recombinant means to generate antibodies containing human specific and recognizable sequences. See, for review, Holmes, et al., J. Immunol., 158:2192–2201 (1997) and Vaswani, et al., Annals Allergy, Asthma & Immunol., 81:105–115 (1998).

Methods of making antibody fragments are also known in the art (see for example, Harlow and Lane, *Antibodies: A Laboratory Manual*, Cold Spring Harbor Laboratory, New York, (1988), incorporated herein by reference). Antibody fragments of the present invention can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab=monovalent fragments. Alternatively, an enzymatic cleavage using pepsin produces two monovalent Fab=fragments and an Fc fragment directly. These methods are described, for example, in U.S. Pat. Nos. 4,036,945 and No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., *Methods: a Companion to Methods in Enzymology*, Vol. 2, page 97 (1991); Bird, et al., Science 242:423–426 (1988); Ladner, et al, U.S. Pat. No. 4,946,778;and Pack, et al., *Bio/Technology* 11:1271–77 (1993).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*, Vol. 2, page 106 (1991).

The invention further contemplates human and humanized forms of non-human (e.g. murine) antibodies. Such humanized antibodies are chimeric immunoglobulins, immunoglobulin chains or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies can comprise substantially all of at least one, and typically two, variable domains, in which all or substantially all of the CDR regions correspond to those of a non-human immunoglobulin and all or substantially all of the Fv regions are those of a human immunoglobulin consensus sequence. The humanized antibody optimally also will comprise at least a portion of an immunoglobulin constant region (Fc), typically that of a human immunoglobulin. For further details, see: Jones et al., Nature 321, 522–525 (1986); Reichmann et al., Nature 332, 323–329 (1988); Presta, Curr. Op. Struct. Biol. 2, 593–596 (1992); Holmes, et al., J. Immunol., 158:2192–2201 (1997) and Vaswani, et al., Annals Allergy, Asthma & Immunol., 81:105–115 (1998).

The invention also provides methods of mutating antibodies to optimize their affinity, selectivity, binding strength or other desirable property. A mutant antibody refers to an amino acid sequence variant of an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. Preferably, mutant antibodies have at least 80%, more preferably at least 85%, even more preferably at least 90%, and most preferably at least 95% amino acid sequence identity or similarity with the amino acid sequence of either the heavy or light chain variable domain of the reference antibody. One method of mutating antibodies involves affinity maturation using phage display.

Affinity maturation using phage display refers to a process described in Lowman et al., Biochemistry 30(45): 10832–10838 (1991), see also Hawkins et al., J. Mol Biol. 254: 889–896 (1992). While not strictly limited to the following description, this process can be described briefly as involving mutation of several antibody hypervariable regions in a number of different sites with the goal of generating all possible amino acid substitutions at each site. The antibody mutants thus generated are displayed in a monovalent fashion from filamentous phage particles as fusion proteins. Fusions are generally made to the gene III product of M13. The phage expressing the various mutants can be cycled through several rounds of selection for the trait of interest, e.g. binding affinity or selectivity. The mutants of interest are isolated and sequenced. Such methods are described in more detail in U.S. Pat. No. 5,750,373, U.S. Pat. No. 6,290,957 and Cunningham, B. C. et al., EMBO J. 13(11), 2508–2515 (1994).

The invention is therefore directed to a method for selecting antibodies and/or antibody fragments or binding polypeptides. Such a method can include constructing a replicable expression vector encoding a fusion protein comprising an antibody polypeptide and at least a portion of a natural or wild type phage coat protein. The expression vector can also have a transcription regulatory element operably linked to the nucleic acids encoding the fusion protein. The vector is mutated at one or more selected positions within the nucleic acid encoding the antibody polypeptide to form a family or "library" of plasmids containing related nucleic acids, each encoding a slightly different antibody polypeptide. Suitable host cells are transformed with the family of plasmids. The transformed host cells are infected with a helper phage having a gene encoding the phage coat protein and the transformed, infected host cells are cultured under conditions suitable for forming recombinant phagemid particles. Each recombinant phagemid displays approximately one copy of the fusion protein on the surface of the phagemid particle.

To screen the phagemids phagemid particles are contacted with an epitope or antigen of the invention. Phagemid particles that bind are separated from those that do not bind the epitope or antigen. Preferably, further rounds of selection are performed by separately cloning phagemids with acceptable binding properties and re-testing their binding affinity one or more times. The plasmids from phagemid particles that appropriately bind the epitope or antigen can also be isolated, cloned and even mutated again to further select for the antibody properties desired, e.g. with good binding affinity.

The method is applicable to polypeptide complexes that are composed of more than one subunit polypeptides. In this case, a nucleic acid encoding each subunit of interest is separately fused to a phage coat protein and separately analyzed for its binding properties.

Any cloning procedure used by one of skill in the art can be employed to make the expression vectors used in such affinity maturation/phage display procedures. For example, one of skill in the art can readily employ known cloning procedures to fuse a nucleic acid encoding an antibody hypervariable region to a nucleic acid encoding a phage coat protein. See, e.g., Sambrook et al., Molecular Cloning, A Laboratory Manual, Cold Spring Harbor Laboratory, N.Y., 1989;Sambrook et al., Molecular Cloning, A Laboratory Manual, Cold Spring Harbor Laboratory, N.Y., 2001.

The antibodies of the invention are isolated antibodies. An isolated antibody is one that has been identified and separated and/or recovered from a component of the environment in which it was produced. Contaminant components of its production environment are materials that would interfere with diagnostic or therapeutic uses for the antibody, and may include enzymes, hormones, and other proteinaceous or nonproteinaceous solutes. The term "isolated antibody" also includes antibodies within recombinant cells because at least one component of the antibody's natural environment will not be present. Ordinarily, however, isolated antibody will be prepared by at least one purification step.

If desired, the antibodies of the invention can be purified by any available procedure. For example, the antibodies can be affinity purified by binding an antibody preparation to a solid support to which the antigen used to raise the antibodies is bound. After washing off contaminants, the antibody can be eluted by known procedures. Those of skill in the art will know of various techniques common in the immunology arts for purification and/or concentration of polyclonal antibodies, as well as monoclonal antibodies (see for example, Coligan, et al., Unit 9, *Current Protocols in Immunology*, Wiley Interscience, 1991, incorporated by reference).

In preferred embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequentator; or 3) to homogeneity by SDS-PAGE under reducing or non-reducing conditions using Coomasie blue or, preferably, silver stain.

Methods of Use

The present invention also relates to diagnostic assays and methods, both quantitative and qualitative for detecting, diagnosing, monitoring, and staging bacterial infections by comparing levels of lipocalin in a mammal or human patient with levels of lipocalin in a normal or uninfected mammalian or human control.

For purposes of the present invention, what is meant by lipocalin levels is, among other things, native protein expressed by a lipocalin gene from the mammal or human to be tested. The native lipocalin protein being detected may be whole protein, a breakdown product, a complex of proteinaceous molecules or a chemically modified protein. A polypeptide comprising SEQ ID NO:1 is one example of a native human lipocalin protein that may be detected using the methods of the invention. A normal human control as used herein includes a human patient without a bacterial infection or samples taken from the patient when the patient was not infected with bacteria.

Levels of native lipocalin are determined in at least one sample of cells, tissues and/or bodily fluids. Thus, for example, a diagnostic assay in accordance with the invention for diagnosing whether elevated levels of lipocalin protein exist can involve comparing a test sample of bodily fluids, cells, or tissues to a normal (uninfected) control sample of bodily fluids, cells, or tissues. Heightened or elevated levels of lipocalin in the test sample, relative to the control sample, are indicative of the presence of a bacterial infection in the mammal from which the test sample was taken.

In a quantitative diagnostic assay of the invention, a positive result indicating the patient being tested has a bacterial infection is one in which cells, tissues or bodily fluid levels of native lipocalin are at least two times higher, or at least five times higher, than in the same cells, tissues or bodily fluid of a normal human control.

Any sample suspected of containing lipocalin may be tested in accordance with the methods set forth herein. Such samples can be samples of cells, tissues and/or bodily fluids. Often, the samples to be tested are bodily fluids such as blood, serum, urine, tears, saliva and the like. In addition to human samples, samples may be taken from mammals such as non-human primates, farm animals, domestic pets, cattle, horses, sheep, swine, etc.

Due to the sensitivity of the test described, it is possible to dilute the sample prior to testing. Dilution can proceed by addition of any fluid compatible with each of the samples to be tested and the antibodies to be used. Serum, when used as the sample, can, for example, be diluted with one or more fluids selected from the group consisting of phosphate-buffered saline, pH 7.0–7.4 (hereinafter, "PBS"), PBS-containing TWEEN 20™ (hereinafter, "PBS T"); PBS T with thimerosal (hereinafter, "PBS TT"), PBS TT with gelatin (hereinafter, "PBS TTG"), and PBS TTG with bovine gamma globulin (hereinafter, "PBS TTGG"). Dilutions may vary as needed, for example, from about 1:10 to about 1:10,000.

Bacterial infections that can be detected by the present cyclic peptides include infections by any target microbial organisms that can infect a mammal or other animal. Such microbial organisms include essentially any single cell organism or parasite that has a cellular membrane and that can infect an animal, including mammals. For example, such microbial organisms include bacteria, fungi, yeast strains and other single cell organisms.

Hence, for example, infections of the following target microbial organisms can be detected by the present antibodies: *Aeromonas* spp., *Bacillus* spp., *Bacteroides* spp., *Campylobacter* spp., *Clostridium* spp., *Enterobacter* spp., *Enterococcus* spp., *Escherichia* spp., *Gastrospirillum* sp., *Helicobacter* spp., *Klebsiella* spp., *Salmonella* spp., *Shigella* spp., *Staphylococcus* spp., *Pseudomonas* spp., *Vibrio* spp., *Yersinia* spp., and the like. Infections that can be detected by the present antibodies include those associated with staph infections (*Staphylococcus aureus*), typhus (*Salmonella typhi*), food poisoning (*Escherichia coli*, such as O157:H7), bascillary dysentery (*Shigella dysenteria*), pneumonia (*Psuedomonas aerugenosa* and/or *Pseudomonas cepacia*), cholera (*Vivrio cholerae*), ulcers (*Helicobacter pylori*) and others. *E. coli* serotype 0157:H7 has been implicated in the pathogenesis of diarrhea, hemorrhagic colitis, hemolytic uremic syndrome (HUS) and thrombotic thrombocytopenic purpura (TTP). The antibodies of the invention can also detect drug-resistant and multiply-drug resistant strains of bacteria, for example, multiply resistant strains of *Staphylococcus aureus* and vancomycin-resistant strains of *Enterococcus faecium* and *Enterococcus faecalis*.

Any immunoassay procedure known to one of skill in the art can be utilized to detect microbial infections by detecting lipocalin with the antibodies of the invention. For example, such immunoassays can involve, one, two or even three of the present antibodies. The immunoassays can be performed in solution or on a substrate, for example, where the antibody is bound to a solid surface. Examples of immunoassays that can be adapted for use in detecting lipocalin with the antibodies of the invention include enzyme-linked immunoassays such as ELISA assays, surface plasmin resonance assays, radioimmunoassays, immunohistochemical assays, and the like.

Appropriate antibody pairs for sandwich immunoassays can be selected from among the antibody preparations of the invention. Such an antibody pair comprises a first high affinity antibody preparation and a second high affinity antibody preparation. In "sequential" sandwich assays, an immobilized antibody can be used to bind the target antigen (lipocalin), the unbound portions of test sample are removed, the bound antigen is used to adsorb a second antibody, and the bound and unbound material is then separated. The amount of bound second antibody is directly proportional to the amount of target antigen in the test sample. In a "simultaneous" sandwich assay, the test sample is not separated before adding the second antibody. Antibodies selected by the methods of the invention need not be used only in "sequential" sandwich assays—they can be used advantageously in simultaneous sandwich assays that require fewer steps and little or no washing during the detection procedure.

In one embodiment, a surface plasmon resonance (SPR)-based sensor system is used. SPR is a useful tool for measuring the interactions between two or more molecules in real time without the use of any detection labels. McDonnell, J. M. (2001) "Surface plasmon resonance towards an understanding of the mechanisms of biological molecular recognition" *Curr. Opin. Chem. Biol.*, 5, 572–577. SPR technology is based on an optical phenomenon, where the response depends on a change in refractive index in the near vicinity of the sensor chip surface employed and the response is proportional to the mass of analyte bound to the surface. SPR is able to continuously analyze every step of an interaction whereas other methods may not allow analysis of the results until the final step is completed. Continuous flow technology can therefore be utilized with the continuous monitoring system offered by SPR.

In general, SPR is used as follows. A selected antibody preparation is immobilized on the sensor surface (substrate) and then the immobilized antibody is contacted with a test solution that may contain lipocalin. This solution flows continuously over the sensor surface. A second antibody that is reactive against lipocalin can be used for detection of a first complex formed between the immobilized antibody and any lipocalin in the test solution. The SPR response or signal increases as more antigen molecules or antigen-antibody complexes from the solution bind to the immobilized antibody on the surface of the sensor.

The SPR angle is sensitive to the composition of the layer at the gold surface of the biosensor chip. A baseline SPR response is therefore first determined by running a buffer over the surface of the antibody-immobilized chip. The binding of antigen to one or two antibodies causes an increase in the refractive index at the surface, thereby changing the SPR angle because it is directly proportional to the amount of bound antigen. The affinities of interest are usually quite strong in biological systems, and binding probes with molecular weights greater than 200 daltons can usually be detected quite accurately. Generally, the SPR is a sensitive technique that requires smaller sample sizes and less run time than many other techniques.

SPR also allows monitoring of both association and dissociation phases during the antibody-antigen interactions (Myszka, 1997;Ohlson et al, 1997). A typical sensorgram consists of a baseline signal (with no change in response units (RU) over time) and an association phase after sample injection, which produces an increase in response units over time. If the reaction rates are fast enough, it is possible to reach a steady state level, where the rates of association and dissociation are equal. Resumed buffer flow causes the complex to dissociate, and the kinetics of dissociation can be recorded. Thus, both association and dissociation kinetics can be measured. At a desired time, a regeneration solution can be injected to remove antigen bound to the surface, and the original response unit value is re-established.

Several candidate antibody preparations with good to excellent or high affinity for the target antigen are therefore selected for use with the SPR immunoassays. From among the group of these high affinity antibody preparations, at least one high affinity antibody preparation is selected for immobilization to a suitable substrate.

The selected antibodies are immobilized on a suitable substrate by any method available to one of skill in the art. The antibody can be linked directly to a selected functional group on the substrate. Alternatively, the antibodies can be linked indirectly to the substrate via a linker or spacer.

For example, the selected antibody can be immobilized via linkage to streptavidin (or biotin) and then attachment to the substrate via a biotin (or streptavidin) moiety that is covalently linked to the substrate. Alternatively, a multilayer of thin films of streptavidin/biotin can be used with an appropriate SPR substrate. A thin film of gold can be evaporated onto a substrate, and a layer of biotin is immobilized onto the film. A monolayer of streptavidin is then immobilized onto the biotinylated gold surface. Streptavidin is a tetravalent protein obtained from *Streptomyces avidinii* that possesses four biotin-binding sites arranged in pairs on opposite faces of the molecule. Once the streptavidin film binds to the biotinylated gold surface, it can be used as a linking molecule to bind to a biotinylated antibody. See Morgan, H. and D. M. Taylor, "A Surface Plasmon Resonance Immunosensor Based on the Streptavidin-Biotin Complex," Biosens. & Bioelect., 7, (1992), pages 405–410; Taylor, D. M., et al,. "Characterization of Chemisorbed Monolayers by Surface Potential Measurements," J. Phys, D:Appl. Phys., 124, (1991), pages 443–450.

Alternatively, a thiol-terminal silane is used for coating of the substrate surface, and a heterobifunctional crosslinker, N-gamma-maleimidobutyryloxy succinimide ester (GMBS) is used for protein attachment. The thiol-terminal silane can be mercaptopropyl trimethoxysilane (MTS). The GMBS reacts at one end with thiol groups present on the silane coating, and at the other end with terminal amino groups of the antibody. See U.S. Pat. No. 5,077,210. With this method, antibodies can be immobilized at a high density (e.g., 2 ng/mm$^2$). The relative amounts of antigen bound by the immobilized antibody can be 3 to 4 times higher than those obtained with some other antibody-immobilization methods. The amount of nonspecific binding to the substrate can be reduced to 2 to 5% of the total binding by addition of blocking agents (BSA, ovalbumin, sugars, dextran, etc.). With this low background, antigen binding can be measured at levels as low as 150 femtomoles when an antigen concentration of 3 picomoles/ml is applied. Antibodies immobilized by this method can maintain their bioactivity for over 18 months.

In order to utilize this technology, a thin (e.g., about 50 angstroms) layer of SiO$_2$ can be deposited on the metal film that coats the substrate. Because the sensing evanescent field of the surface plasmon resonance roughly extends to about 1 µm above the metal film, this SiO$_2$ layer will probably not adversely affect sensitivity. If the SiO$_2$ layer sufficiently passivates the metal film surface, silver films could more advantageously be used. Silver films typically can produce more sensitive SPR biosensors than chemically inert gold films.

Another type of surface immobilization technique uses polymer hydrogel matrices. These materials typically contain a large amount of water, are soft, and are bioinert. Examples include cross-linked polymer films of poly(vinyl alcohol) and films of carboxymethyldextran. See Kobayashi, J. and Y. Ikada, "Covalent Immobilization of Proteins Onto the Surface of Poly(vinyl alcohol) Hydrogel," Biomaterials, 12, (1991), pages 747–751;Johnsson, B. et al, "Immobilization of Proteins to a Carboxymethyldextran-Modified Gold Surface for Biospecific Interaction Analysis in Surface Plasmon Resonance Sensors," Anal. Biochem., 196, (1991), 268–277;Lofas, S. and B. Johnsson, "A Novel Hydrogel Matrix on Gold Surfaces in Surface Plasmon Resonance Sensors for Fast and Efficient Covalent Immobilization of Ligands," J. Chem. Soc. Commun., (1990), pages 1526–1528.).

In order to apply a matrix of carboxymethyldextran, a monolayer of long chain 1,ω-hydroxyalkyl thiols is used to form a hydrophilic surface on a gold substrate. This metal protection layer serves partly to prevent proteins from contacting the metal surface, and partly to facilitate carboxymethyldextran binding. The carboxyl-modified carboxymethyldextran hydrogel is deposited by a series of steps that results in a negatively charged matrix to which a variety of antibodies can be covalently bound.

After immobilization of a selected antibody onto a suitable substrate, the reactivity of the immobilized antibody with antigen can be tested to insure that antibody-antigen affinity has not been adversely affected by immobilization of the antibody on the sensor chip. SPR requires small quantities of materials, and a sensor chip with immobilized antibody can typically be used for more than 100 analysis cycles. The chip surface can be regenerated with mild acidic or basic solutions. Several gentle cocktail solutions are available for regeneration (Andersson, 1999).

Accordingly, the invention provides a method of detecting lipocalin in a test sample by contacting a test sample with a biosensor comprising an antibody capable of selectively binding to at least one epitope on the lipocalin. A second antibody capable of selectively binding to a second epitope on lipocalin can also be provided, where the assay will then involve detecting formation of a ternary antibody-antigen-antibody complex on the biosensor.

Kits

The present invention provides a kit for detecting lipocalin, which is applicable for practicing of the methods of the present invention. The kit comprises an antibody specific to a lipocalin loop peptide, for example, a peptide having any one of SEQ ID NO:2–14 as well as variants and derivatives thereof. Detection of lipocalin can be carried out using the antibody in any immunological assay available to one of skill in the art.

When two antibodies sandwich ELISA is employed as the immunological assay, the kit may comprise first and second antibodies specific to lipocalin. The second antibody is preferably capable of binding to a conjugate of lipocalin and the first antibody. For this purpose, for example, an antibody that recognizes an epitope different from that recognized by the first antibody may be used as the second antibody.

The kit of the present invention may further comprise a substance and/or a device suitable for the detection of antibodies, the immobilization of antibodies, and the like. To immobilize the antibody, the kit may further comprise a carrier (e.g., a microtiter plate or a substrate appropriate for surface plasmon resonance), a solution for the immobilization and a blocking solution (e.g., gelatin-containing PBS). For ease in detecting antibody-antigen complexes, it is preferable that the antibodies be labeled. In this case, the kit may further comprise a detecting reagent for detecting the label. For example, when biotin is used as the labeling substance, the detecting reagent may comprise a conjugate of streptavidin with horseradish peroxidase (HRP) as well as a color-developing solution that is capable of developing a color by the action of HRP.

In another embodiment, the invention provides kits comprising a biosensor chip with an immobilized first antibody, for example, an antibody reactive with any one of SEQ ID NO:2–14. Such a kit can also contain a container with a second antibody preparation of the invention and instructions for using such a chip to detect lipocalin. The kit can also contain a container with a negative control sample (e.g. components frequently encountered in samples that contain lipocalin); a container with a positive control sample (e.g., a solution of lipocalin at a specific, known concentration); and/or a container with sample diluent.

To use the kits of the present invention, a sample is diluted in sample diluent (if necessary), and then placed in contact with the first antibody (e.g. immobilized on a chip) for a time and under conditions for any lipocalin present in the sample to bind to the first antibody. The sample can also be contacted with a second antibody preparation. The binding is then detected, for example, with a Biacore SPR instrument.

The invention will be described in more detail with reference to the following Examples. However, it should be

```
1. Pro17 to Gln28:   PLQQNFQDNQFQ   (SEQ ID NO: 2)

2. Asn39 to Tyr52:   NAILREDKDPQKMY (SEQ ID NO: 3)

3. Lys59 to Ser63:   KEDK           (SEQ ID NO: 4)

4. Arg72 to Lys75:   RKKK           (SEQ ID NO: 5)

5. Gly86 to Gly90:   GCQPG          (SEQ ID NO: 6)

6. Gly95 to Gly102:  GNIKSYPG       (SEQ ID NO: 7)

7. Asn114 to Gln117: NYNQ           (SEQ ID NO: 8)

8. Phe168 to Asp177: FPVPIDQCID     (SEQ ID NO: 9)
```

Any peptide within SEQ ID NO:2–9 can be used as an antigen for generating polyclonal or monoclonal antibodies that are specific to lipocalin. In addition two opposing loops from different sides of the lipocalin molecule can be chosen such that the resulting antibodies can be used to capture lipocalin in a diagnostic assay, that is, they are capable of forming a sandwich structure. For example, raising antibodies against loops 1 and 2 or 4 and 5, could be employed. It may also be desirable to include one or two flanking residues on each side of smaller loops in order to increase their antigenicity (for example when using loop 3).

Four loop regions (1, 2, 3, and 8) were picked to raise monoclonal antibodies. The specific peptides synthesized were:

```
Loop 1: CLSKVPLQQNFQDNQ   (residues 12 to 26)   (SEQ ID NO: 10)

Loop 2: CGNAILREDKDPQKMY  (residues 37 to 52)   (SEQ ID NO: 11)

Loop 3: YELKEDKS          (residues 56 to 63)   (SEQ ID NO: 12)

Loop 8: FPVPIDQCID        (residues 168 to 177) (SEQ ID NO:  9)
``` understood that the invention is not limited to the specific details set forth in the Examples.

EXAMPLE 1

HNL Loop Regions as Antigens for Producing Antibodies

The amino acid sequence of human neutrophil gelatinase-associated lipocalin is as follows (SEQ ID NO:1).

```
  1 QDSTSDLIPA PPLSKVPLQQ NFQDNQFQGK WYVVGLAGNA

41 ILREDKDPQK MYATIYELKE DKSYNVTSVL FRKKKCDYWI

81 RTFVPGCQPG EFTLGNIKSY PGLTSYLVRV VSTNYNQHAM

121 VFFKKVSQNR EYFKITLYGR TKELTSELKE NFIRFSKSLG

161 LPENHIVFPV PIDQCID
```

Lipocalin contains eight surface-accessible loops. These areas are shown as thin yellow bands in FIG. 1. Two of these loops flank the central lipocalin beta barrel. The loop areas make good epitope targets because they are solvent exposed. The sequences of the loop regions are as follows:

Although any contiguous number of amino acids within each loop region (with or without flanking sequences) could be used to generate antibodies against that portion of lipocalin.

A BLAST search of the four sequences (using the NCBI BLAST server) revealed no significant sequence matches to known protein sequences other than to lipocalin. This indicates that the antibodies raised against these sequences will be highly specific for lipocalin.

EXAMPLE 2

Antibody Generation

This Example illustrates that specific lipocalin peptides can be used to generate antibodies that are reactive with lipocalin.

Peptides

Peptides were chosen based upon the loop regions of human neutrophil lipocalin described in the X-ray crystallographic structure published by Goetz et al. Biochemistry 2000, 39, 1935–1941. Specific peptides were chosen for conjugation to KLH protein. These peptides had the following sequences:

SEQ ID NO: 12 - YELKEDKS

SEQ ID NO: 13 - LSKVPLQQNFQDNQ

SEQ ID NO: 14 - GNAILREDKDPQKMY

SEQ ID NO: 9 - FPVPIDQCID

KLH-conjugated peptides were synthesized and purified by HPLC by SigmaGenesis. Specifically, peptides having SEQ ID NO:12, 13 and 14 were synthesized with an N-terminal cysteine residue such that the peptide could be conjugated to KLH using succinimidyl m-maleimidobenzoate (MBS) as a coupling reagent. The peptide having SEQ ID NO:9 (FPVPIDQCID) was conjugated to KLH using activated EDC (1-ethyl-3(3-dimethylaminopropyl)carbonyldiimide hydrochloride) chemistry, such that the peptide was linked via the free amine.

Production of Antibodies

Balb/c mice were immunized with KLH-conjugated peptides (100 μg per injection). On day zero, 100 μg of conjugated peptide was emulsified with complete Fruend's adjuvant (CFA) and injected intraperitoneally into Balb/c mice. Four mice were separately immunized against the two conjugated peptides, so that a total of eight mice were immunized. Booster immunizations were given on days 21, 70, and 92 using 100 μg of conjugated peptide emulsified with incomplete Fruend's adjuvant (IFA).

Materials for ELISA Tests

Anti-mouse IgG and IgM peroxidase-labeled antibodies were purchased from Kirkegaard and Perry Laboratories (KPL). Anti-MMP-9 (Ab-1) IgG antibodies were purchased from Oncogene Research Products. Anti-α-tubulin IgM antibodies were purchased from Santa Cruz Biotechnology. The C-reactive protein (CRP) IgG antibodies were purchased from Biospacific. Matrix metalloproteinase-9 complexed with HNL (MMP-9/HNL) was purchased from Calbiochem. Alpha-tubulin was purchased from Cytoskeleton. CRP antigen was purchased from Fitzgerald Industries International.

ELISA Tests

ELISA assays were developed by first incubating the specific peptide or protein in sodium carbonate buffer, pH 9.0 in 96-well ELISA plates overnight at 4° C. For KLH-conjugated peptides, 50 μL of an approximate 2 μg/mL solution was placed in each well. Somewhat lower concentrations of purified peptides and the control proteins including C-reactive protein (CRP), matrix metalloproteinase-9 complexed with HNL (MMP-9/HNL) and α-tubulin were used. In particular, 50 μL of an approximate 1 μg/mL solution of such purified peptides and the control proteins were placed in the designated wells. After the overnight incubation, the solutions were removed, and wells were treated with 200 μL of blocking buffer (PBS with 0.02% sodium azide, 1% bovine serum albumin) overnight at 4° C. The blocking solution was removed, and wells were washed once with PBS with 0.02% sodium azide. The wash solution was tapped out of the plates for the ELISA assay.

Fifty microliters of a 1:30 dilution of test serum from immunized Balb/c mice in blocking buffer was incubated in each well for 1 hour at room temperature. The solutions were removed, and the plates were washed three times with PBS containing Tween 20. A 1:1000 solution of anti-mouse IgG-HRP (horseradish peroxidase) conjugated antibody or a 1:500 anti-mouse IgM-HRP conjugated antibody in blocking buffer was added to each well (200 μL) for 1 hour at room temperature. The solutions were removed, and the plates were washed three times with PBS containing Tween 20. TMB solution (100 μL) was added to each well for 5–10 minutes. TMB stop solution (100 μL) was added to each well to quench the reaction. Wells were read on a plate reader at 450 nm.

Positive controls used to verify that the ELISAs were working properly included an anti-MMP-9 IgG mouse antibody (1:1000), an anti-CRP IgG mouse antibody (1:1000), and an anti-α-tubulin IgM mouse antibody (1:1000). For negative controls, blocking buffer was added to each well containing the different antigens. The absorbance at 450 nm for the negative controls was subtracted from the test samples. These data are shown in FIGS. 2 and 3.

Results

Two of the KLH-conjugated peptides were used (CG-NAILREDKDPQKMY, SEQ ID NO:11;FPVPIDQCID, SEQ ID NO:9) for the in vivo immunizations in Balb/c mice. Serum samples were obtained twelve weeks after initiation of immunizations. Serum samples were tested using the established ELISA assays as described above. Two serum samples (#60 immunized with KLH-SEQ ID NO:11; #70 immunized with KLH-SEQ ID NO:9) showed positive ELISA results with both IgG and IgM secondary antibodies (FIGS. 2 and 3).

Figure 2:
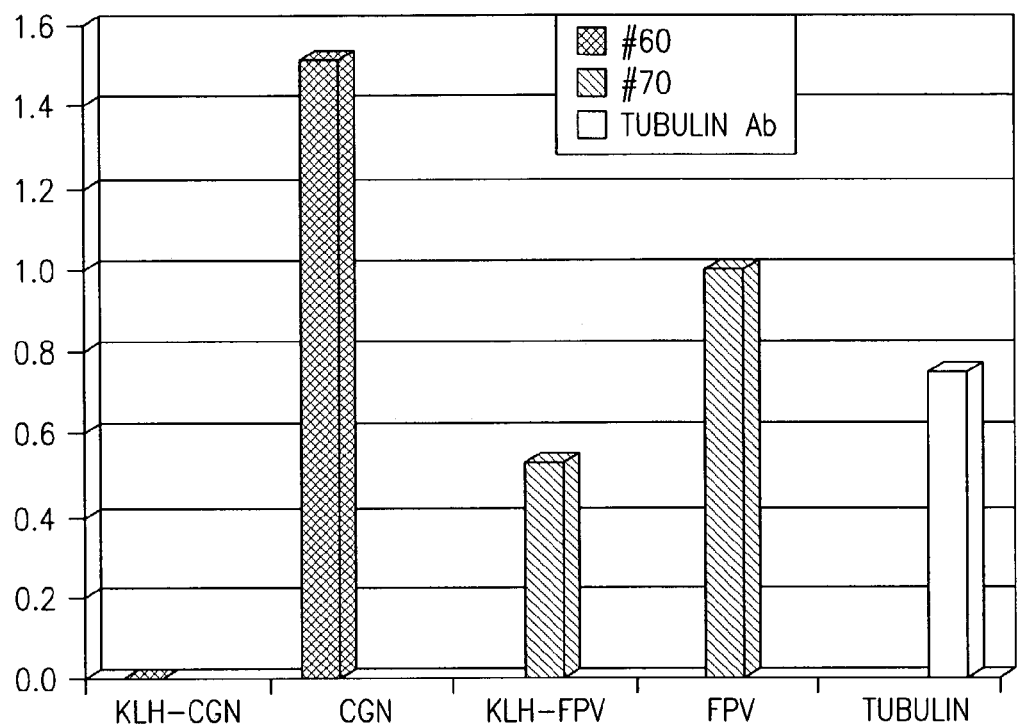
FIG. 2 provides a bar graph illustrating the increase in absorbance at 450 nm for ELISA assays of different antibody preparations using an IgM-Horse radish peroxidase secondary antibody. The type of antigen adsorbed to the ELISA plates is identified along the X-axis, where KLH-CGN is the SEQ ID NO:11 peptide conjugated to KLH, CGN is the unconjugated SEQ ID NO:11 peptide, KLH-FPV is the SEQ ID NO:9 peptide conjugated to KLH, FPV is the unconjugated SEQ ID NO:9 peptide, and tubulin is the α-tubulin positive control. The #60 antibody preparation (bars with cross-hatching) was prepared by immunization with the SEQ ID NO:11 peptide conjugated to KLH. The #70 antibody preparation (bars with diagonal slashes) was prepared by immunization with the SEQ ID NO:9 peptide conjugated to KLH. The tubulin antibody (white bars) preparation was prepared by immunization with α-tubulin. The absorbance of the negative control has been subtracted from the test and control absorbance values provided in the graph.
Figure 3:
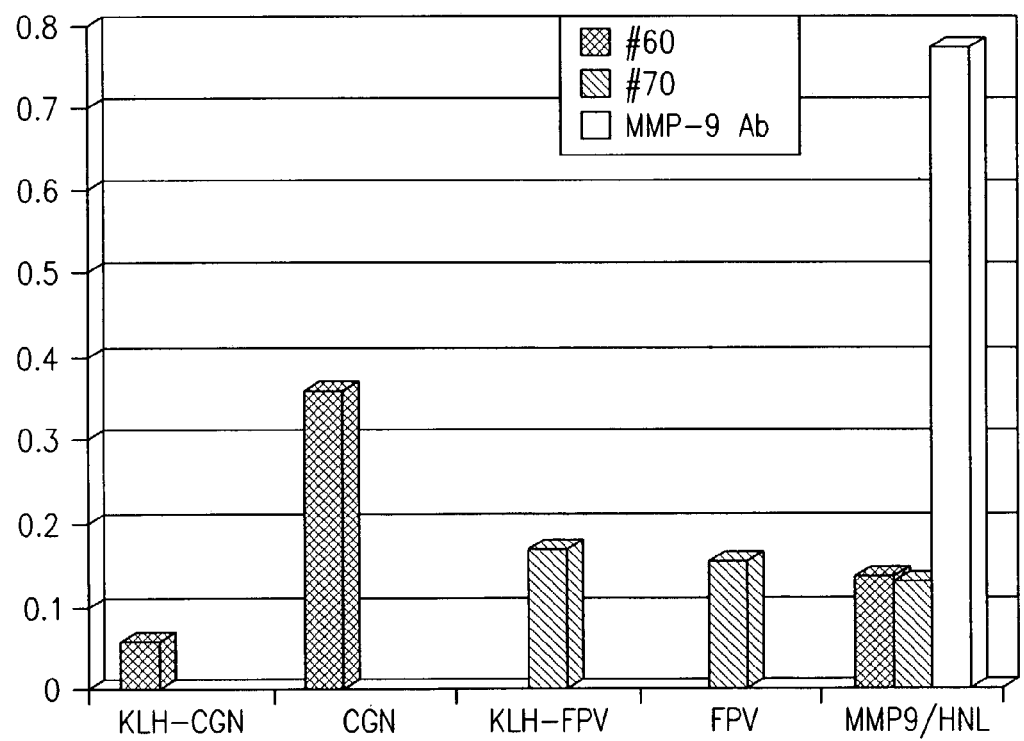
FIG. 3 provides a bar graph illustrating the increase in absorbance at 450 nm for ELISA assays of different antibody preparations using an IgG-Horse radish peroxidase secondary antibody. The type of antigen adsorbed to the ELISA plates is identified along the X-axis, where KLH-CGN is the SEQ ID NO:11 peptide conjugated to KLH, CGN is the unconjugated SEQ ID NO:11 peptide, KLH-FPV is the SEQ ID NO:9 peptide conjugated to KLH, FPV is the unconjugated SEQ ID NO:9 peptide, and MMP-9/HNL is metalloproteinase-9 conjugated to HNL (positive control). The #60 antibody preparation (bars with cross-hatching) was prepared by immunization with the SEQ ID NO:11 peptide conjugated to KLH. The #70 antibody preparation (bars with diagonal slashes) was prepared by immunization with the SEQ ID NO:9 peptide conjugated to KLH. The MMP-9/HNL antibody (white bars) preparation was prepared by immunization with MMP-9/HNL. The absorbance of the negative control has been subtracted from the test and control absorbance values provided in the graph.

FIGS. 2 and 3 describe the increase in absorbance at 450 nm over the negative control found in the IgM (FIG. 2) and IgG (FIG. 3) ELISA results. Serum sample #60 showed both a strong IgG and a strong IgM response with the free CGN (SEQ ID NO:11) peptide and a weak positive response with the KLH-conjugated CGN (SEQ ID NO:11) peptide. Serum sample #70 had strong IgG and IgM responses for both the free SEQ ID NO:9 peptide and the KLH-conjugated SEQ ID NO:9 peptide. Moreover, both serum samples had a positive response to the MMP-9/HNL complex, suggesting that IgG antibodies present in the sera can bind to HNL as it is complexed with MMP-9. Neither of the two positive serum samples displayed cross-reactivity to the other KLH-conjugated peptide or the other free peptide, suggesting that the antibody present in the serum is not binding to the KLH protein itself but to the linked peptide. These data indicate that this approach is useful for generating antibodies to HNL.

EXAMPLE 3

Hybridoma Cell Lines that Produce Monoclonal Antibodies

This Example illustrates that monoclonal antibodies can readily be prepared that are reactive with selected lipocalin epitopes.

Methods

Methods available in the art were utilized for in vitro and in vivo manipulation of monoclonal antibodies. Briefly, hybridoma cell lines expressing monoclonal antibodies were made by fusing B-cells from an in vivo-immunized mouse spleen with mouse myeloma cells using polyethylene glycol. Hybridoma cells were plated in several 96-well plates and were kept in culture for two weeks. Cell lines were screened for monoclonal antibodies using the ELISA method described above.

Results

Supernatants (50 µL) were removed from each of 1032 wells containing hybridoma cells created from myeloma cells and B-cells from mouse #60 (immunized with KLH-SEQ ID NO:11). These supernatants were tested for monoclonal antibodies using the aforementioned ELISA test using plates coated with CGNAILREDKDPQKMY, SEQ ID NO:11. The results are provided in Table 1.

TABLE 1

| Plate Number, Well Number | A (450 nm) |
| --- | --- |
| α-Tubulin Positive Control | 0.358 |
| Media Negative Control | 0.068 |
| Plate #2, D12 | 0.186 |
| Plate #3, A12 | 0.179 |
| Plate #3, B12 | 0.224 |
| Plate #3, D12 | 0.226 |
| Plate #3, E12 | 0.168 |
| Plate #3, F12 | 0.140 |
| Plate #3, G12 | 0.170 |
| Plate #3, H12 | 0.154 |
| Plate #4, A4 | 0.150 |
| Plate #4, A9 | 0.143 |
| Plate #4, E4 | 0.135 |
| Plate #4, F10 | 0.135 |
| Plate #4, F11 | 0.158 |
| Plate #4, G11 | 0.194 |
| Plate #5, H2 | 0.177 |
| Plate #6, H12 | 0.168 |
| Plate #7, B12 | 0.171 |
| Plate #7, H12 | 0.175 |
| Plate #8, E12 | 0.306 |
| Plate #10, B4 | 0.151 |
| Plate #10, E8 | 0.144 |
| Plate #10, F3 | 0.181 |
| Plate #10, H4 | 0.147 |

Of the 1032 supernatants tested, twenty-three showed positive ELISA results for IgM antibodies that bind CGNAILREDKDPQKMY, SEQ ID NO:11. These data indicate that this approach is useful for generating antibodies to HNL.

REFERENCES

1. Cole, T. B; Smith, S. J.; Buchanan, G. R. "Haematological Alterations During Acute Infection in Children with Sickle Cell Disease," Pediatr. Infect. Dis. J. 1987, 6, 454–457.
2. Mellors, J. W; Horwitz, R. I.; Harvey, M. R.; Horwitz, S. M. "A Simple Index to Identify Occult Bacterial Infection in Adults with Acute Unexplained Fever," Arch. Intern. Med. 1987, 147, 666–671.
3. Logdberg, Lennart; Wester, Lena. "Immunocalins: A Lipocalin Subfamily that Modulates Immune and Inflammatory Responses," Biochimica et Biophysica Acta 2000, 1482, 284–297.
4. Xu, Shengyuan; Venge, Per. "Lipocalins as Biochemical Markers of Disease," Biochimica et Biophysica Acta 2000, 1482, 298–307.
5. Xu, S. Y.; Petersson, C. G. B; Carlson, M.; Venge, P. "The Development of an Assay for Human Neutrophil Lipocalin (HNL)—to be used as a Specific Marker of Neutrophil Activity In Vivo and In Vitro," Journal of Immunological Methods 1994, 171, 245–252.
6. Blaser, Jorg; Triebel, Susanne; Tschesche, Harald. "A Sandwich Enzyme Immunoassay for the Determination of Neutrophil Lipocalin in Body Fluids," Clinica Chimica Acta 1995, 235, 137–145.
7. Xu, S. Y.; Pauksen, K.; Venge, P. "Serum Measurements of Human Neutrophil Lipocalin (HNL) Discriminate between Acute Bacterial and Viral Infections," Scand. J. Clin. Lab. Invest. 1995, 55, 125–131.
8. Goetz, David H.; Willie, Sirkku T.; Armen, Roger S.; Bratt, Tomas; Borregaard, Niels; Strong, Roland K. "Ligand Preference Inferred from the Structure of Neutrophil Gelatinase Associated Lipocalin," Biochemistry 2000, 39, 1935–1941.
9. U.S. Pat. No. 5,866,432 Methods for diagnosis of periodontal diseases.
10. U.S. Pat. No. 6,365,716, Antibodies to lipocalin homologs.
11. U.S. Pat. Nos. 6,020,163 and 6,143,720: Lipocalin homolog.
12. U.S. Pat. No. 6,114,123: Lipocalin family protein.
13. U.S. Pat. No. 6,136,526: Use of human neutrophil lipocalin (HNL) as a diagnostic marker and anti-HNL-antibody preparation.

All publications and patents are incorporated by reference herein, as though individually incorporated by reference. The invention is not limited to the exact details shown and described, for it should be understood that many variations and modifications may be made while remaining within the spirit and scope of the invention defined by the statements.

What is claimed:

1. An isolated antibody that binds to a lipocalin antigen consisting of SEQ ID NO:11.

* * * * *

UNITED STATES PATENT AND TRADEMARK OFFICE
CERTIFICATE OF CORRECTION

| | | |
|---|---|---|
| PATENT NO. | : 7,056,702 B2 | Page 1 of 1 |
| APPLICATION NO. | : 10/320732 | |
| DATED | : June 6, 2006 | |
| INVENTOR(S) | : Stephen Quirk and Julie M. Villanueva | |

It is certified that error appears in the above-identified patent and that said Letters Patent is hereby corrected as shown below:

On the face page, please insert a field (73) to include the assignee --Kimberly-Clark Worldwide, Inc., Neenah, WI (US),--, therfor.

Signed and Sealed this

Seventeenth Day of October, 2006

JON W. DUDAS
*Director of the United States Patent and Trademark Office*